United States Patent
Kloss et al.

(10) Patent No.: US 8,449,577 B2
(45) Date of Patent: May 28, 2013

(54) SPINE FIXATOR

(75) Inventors: Henning Kloss, Ennetburgen (CH); Bjorn Schafer, Ruppichteroth (DE)

(73) Assignee: Henning Kloss, Ennetburgen (CH)

( * ) Notice: Subject to any disclaimer, the term of this patent is extended or adjusted under 35 U.S.C. 154(b) by 539 days.

(21) Appl. No.: 11/815,756

(22) PCT Filed: Feb. 8, 2006

(86) PCT No.: PCT/DE2006/000211
§ 371 (c)(1), (2), (4) Date: Aug. 7, 2007

(87) PCT Pub. No.: WO2006/084443
PCT Pub. Date: Aug. 17, 2006

(65) Prior Publication Data
US 2008/0195159 A1    Aug. 14, 2008

Related U.S. Application Data

(60) Provisional application No. 60/661,927, filed on Mar. 16, 2005.

(30) Foreign Application Priority Data

Feb. 8, 2005 (DE) .......................... 10 2005 005 647

(51) Int. Cl.
*A61B 17/70* (2006.01)
(52) U.S. Cl.
USPC .......................................................... 606/264
(58) Field of Classification Search
USPC ................. 606/246, 264, 265–268, 270, 272, 606/277–279, 295, 301, 302, 304, 305–308, 606/328, 311, 312, 315, 317
See application file for complete search history.

(56) References Cited

U.S. PATENT DOCUMENTS

| | | | | |
|---|---|---|---|---|
| 5,910,142 | A | 6/1999 | Tatar | 606/61 |
| 6,660,005 | B2 * | 12/2003 | Toyama et al. | 606/308 |
| 6,761,719 | B2 | 7/2004 | Justis et al. | |
| 7,635,380 | B2 * | 12/2009 | Zucherman et al. | 606/267 |
| 7,942,900 | B2 * | 5/2011 | Winslow et al. | 606/246 |
| 7,963,978 | B2 * | 6/2011 | Winslow et al. | 606/246 |
| 8,002,800 | B2 * | 8/2011 | Winslow et al. | 606/246 |
| 8,012,175 | B2 * | 9/2011 | Winslow et al. | 606/246 |

(Continued)

FOREIGN PATENT DOCUMENTS

| | | |
|---|---|---|
| DE | 42 43 951 | 7/1994 |
| DE | 196 46 534 | 5/1998 |

(Continued)

*Primary Examiner* — Ellen C Hammond
*Assistant Examiner* — Stuart S Bray
(74) *Attorney, Agent, or Firm* — J.C. Patents

(57) ABSTRACT

The present invention relates to a device for the stabilization of the spine comprising at least two pedicle screws and at least one interjacent linking member. The present invention further relates to pedicle screws which combine the advantages of a monoaxial screw with those of a polyaxial screw by avoiding the drawbacks of these screw types. This objective is achieved due to the fact that the screw head is supported on the screw shank such that it cannot be moved for providing an optimal reducibility of the vertebrae, wherein a movable ball element is present in the screw head, which facilitates the introduction of the linking member and fixates the same once the introduction has been effected.

7 Claims, 9 Drawing Sheets

U.S. PATENT DOCUMENTS

| | | | |
|---|---|---|---|
| 2003/0220642 A1 | 11/2003 | Freudiger | |
| 2004/0260283 A1* | 12/2004 | Wu et al. | 606/61 |
| 2005/0261687 A1* | 11/2005 | Garamszegi et al. | 606/61 |
| 2006/0036244 A1* | 2/2006 | Spitler et al. | 606/61 |
| 2006/0149240 A1* | 7/2006 | Jackson | 606/61 |
| 2006/0155277 A1* | 7/2006 | Metz-Stavenhagen | 606/61 |
| 2006/0241595 A1* | 10/2006 | Molz et al. | 606/61 |
| 2008/0306528 A1* | 12/2008 | Winslow et al. | 606/246 |
| 2010/0234891 A1* | 9/2010 | Freeman et al. | 606/266 |

FOREIGN PATENT DOCUMENTS

| | | |
|---|---|---|
| DE | 100 05 386 | 8/2001 |
| DE | 103 19 183 | 11/2004 |
| EP | 0669109 | 8/1995 |
| JP | 2004-505138 | 2/2004 |
| WO | WO 01/06940 | 2/2001 |
| WO | 03/037216 | 5/2003 |
| WO | WO 03/096915 | 11/2003 |

* cited by examiner

SPINE FIXATOR

CROSS-REFERENCE TO RELATED APPLICATION

This application is a 371 of international application of PCT application serial no. PCT/DE2006/000211, filed on Feb. 8, 2006, which claims the priority benefit of German application no. 10 2005 005 647.4, filed on Feb. 8, 2005 and U.S. provisional application Ser. No. 60/661,927, filed on Mar. 16, 2005. The entirety of each of the above-mentioned patent applications is hereby incorporated by reference herein and made a part of this specification.

BACKGROUND OF THE INVENTION

1. Field of the Invention

The present invention relates to a device for the stabilization of the spine comprising at least two pedicle screws and at least one interjacent linking member. The present invention further relates to pedicle screws possessing a movable ball element in a movable screw head for easier introduction of the linking member, this construction providing an optimal reducibility of the vertebrae while strongly enclosing the linking member.

2. Description of Related Art

In the state of the art, only embodiments which describe a support of the linking member in the screw head of the pedicle screw along the axial axis, which provides a certain flexibility even after the implantation, are known.

Thus, US 2003/0220642 A1 discloses in one embodiment an elastic linking member with a thread and associated pedicle screws with screw heads disposing of a respective thread, so that the linking member can be introduced into the screw heads by rotational movements and is movable along its longitudinal axis.

EP 0 669 109 B1 describes a support device for the spine, which allows less a movement of the linking member along its longitudinal axis than rather a movement of the individual pedicle screws relative to each other. For this purpose, a flexible strip is used as the linking member, and a slightly deformable support element is attached to the strip, wherein the support element abuts on the screw heads of two pedicle screws, respectively.

U.S. Pat. No. 6,761,719 B2 discloses a support device for the spine which allows movements by inserting a shape memory metal as a linking member between the vertebrae which possesses pseudoelastic properties at body temperature.

The embodiments referred to in WO 03/037216 A2 attempt to achieve a flexibility of the linking member by using a flexible linking member which is made for example of polyester, polyethylene, polylactide, or nitinol, and which is fixed in the screw heads of the pedicle screws and possesses absolutely no degrees of freedom of movement within the same.

SUMMARY OF THE INVENTION

The object of the present invention is to provide a device for the stabilization of the spine which can strongly enclose the linking member and which on the other hand allows for an optimal reducibility of the vertebrae.

This object is resolved by providing a pedicle screw having a screw head with two opposite recesses and a ball head with two opposite parallel surfaces which abut on the corresponding parallel surfaces of the screw head while the longitudinal axis which passes through the two opposite recesses of the screw head is perpendicular to the parallel surfaces of the screw head. Further advantageous embodiments, aspects and details of the invention will be described in the dependent claims, the description, the examples and the figures.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
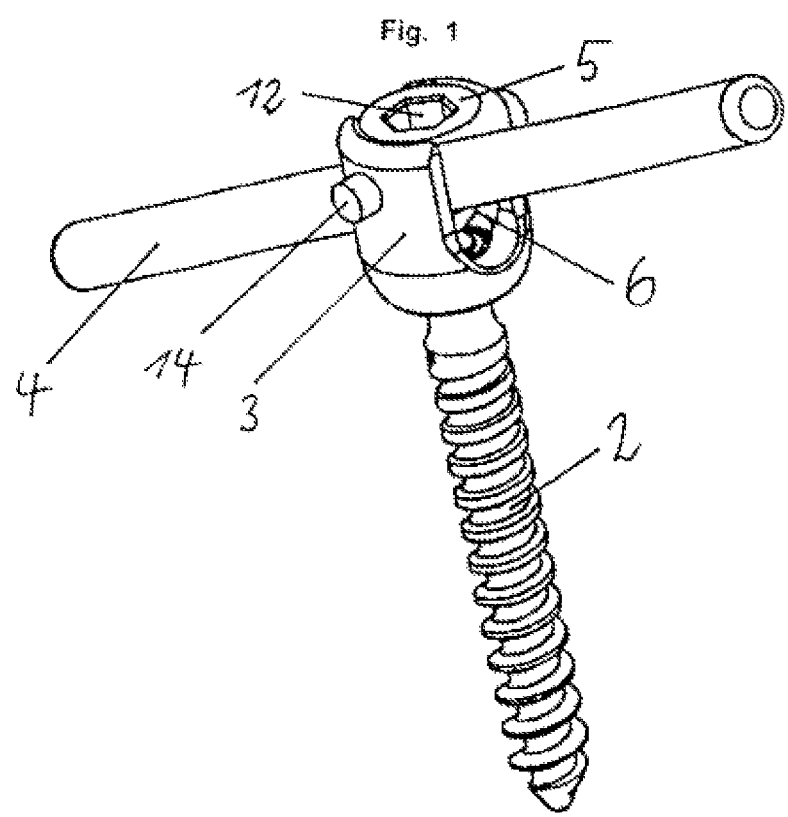
FIG. 1 shows a side view of an embodiment of the pedicle screw 1 according to the invention with inserted linking member 4.

Reference will now be made in detail to the present preferred embodiments of the invention, examples of which are illustrated in the accompanying drawings. Wherever possible, the same reference numbers are used in the drawings and the description to refer to the same or like parts.

The present invention relates to a pedicle screw 1 comprising a screw shank 2 and a screw head 3 having two opposite elongated hole-shape recesses, characterized in that a ball element 6 with a recess for receiving a linking member 4 is supported such that it is movable in the screw head 3. Thus it is achieved that the ball element 6 can be adjusted to the position of the penetrating linking member 4 in the direction of anteflexion/retroflexion and that it can strongly lock said linking member once the fixation has been completed.

The design of the screw shank 2 of the pedicle screw 1 is not essential for the invention and can be any conventional form. The pedicle screws 1 are preferably self-tapping. In a preferred embodiment, the screw shank 2 has a thread with a constant external diameter and with a conically increasing core diameter.

On the contrary, both the design of the screw head 3 of the pedicle screw 1 and that of the ball head 17 of the screw shank 2 are essential. The screw head 3 is hollow and can receive a ball element 6, which makes possible rotational movements of a penetrating linking member 4 in the screw head 3 about the lateral axis. A rotational movement of the penetrating linking member 4 about the lateral axis means that the linking member 4 can be moved in the direction of anteflexion/retroflexion.

For the penetrating linking member 4 can make these movements, the screw head 3 must possess two opposite elongated hole-shape openings within which the linking member 4 are free to tilt or swivel. From this fact results a preferably cylindrical or oval design of the screw head 3. The screw head 3 of the pedicle screw 1 requires only a small volume so that it is possible to screw it in deeply; furthermore the screw head has no sharp edges.

The axes are designated as follows relative to the possible movements of the linking member 4 in the unfixed state. The axis passing along the spine is referred to as axial axis. The anteflexion/retroflexion axis is perpendicular to the axial axis passing through the abdomen and the back of the patient, and the lateral axis is perpendicular to the axial axis and as well perpendicular to the anteflexion/retroflexion axis.

Thus, a rotation of the linking member 4 about the lateral axis, which passes through the screw head 3, causes a movement of the ends of the linking member in the direction of anteflexion/retroflexion and a rotation about the axial axis causes a movement of the longitudinal axis passing through the linking member 4 in lateral direction.

Thus, the ball element 6 permits a movement of the linking member 4 in the unfixed state in the direction of anteflexion/retroflexion. The fact that there is no mobility of the screw head 3 on the screw shank 2 in direction of the axial axis is important for a complete transmission of the leverage from linking member 4 to the pedicle screw and to the vertebral body. Such movements are possible using polyaxial screws, which can reduce the vertebrae in an only suboptimal manner, as will be explained in detail below.

In order that the screw head 3 on the screw shank 2 cannot move along the axial axis but only in direction of the lateral axis, the head 17 of the screw shank 2 is not designed as a ball about which the screw head 3 can make a rotation of 360 degrees. The head 17 of the screw shank 2 is designed as a ball with two opposite surfaces (18a and 18b) being parallel to each other, the screw head 3 having parallel surfaces (18c, 18d) abutting on the surfaces 18a and 18b, respectively. The surfaces 18a and 18b have the same size. The surfaces 18c and 18d have the same size as well, and all surfaces 18a, 18b, 18c and 18d are parallel to each other. Thus, a tilting movement of the screw head 3 on the screw shank 2 is possible, however only in lateral direction, i.e. about the axial axis. Due to this fact, the screw head 3, which is supported on the screw shank 2 according to the invention can make tilting movements only in direction of the lateral axis, i.e. within the plane spanned by the lateral axis and the anteflexion/retroflexion axis, said plane being perpendicular to the axial axis. The screw head 3, which is supported on the screw shank 2, on the other hand cannot be freely rotated about the longitudinal axis of the screw shank 2.

Figure 9:
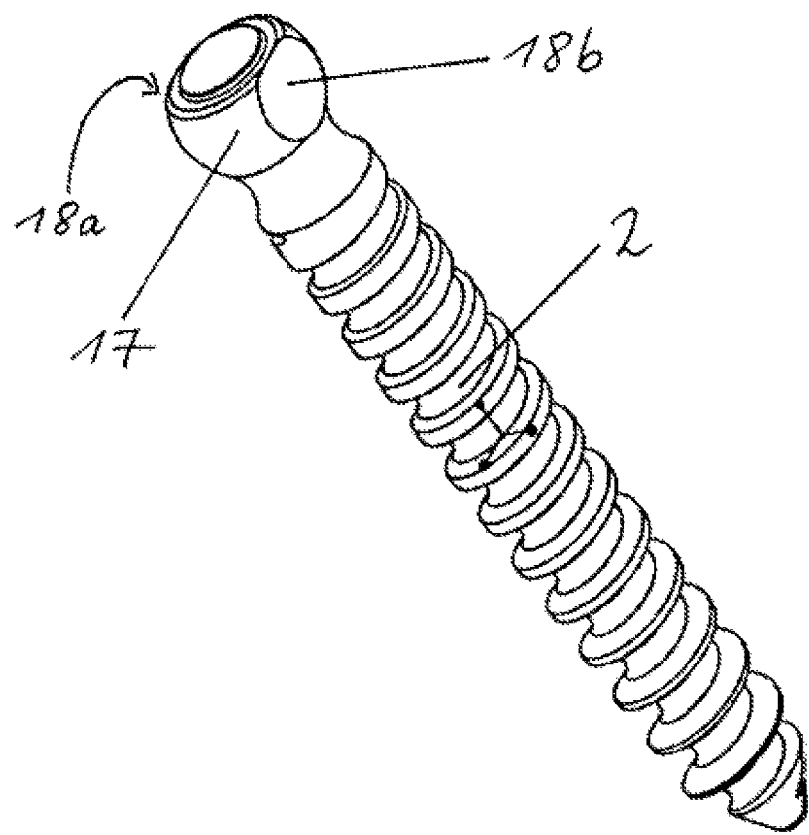
FIG. 9 shows the screw shank 2 with the ball head 17 and the two flat, parallel surfaces 18a and 18b.
Figure 10:
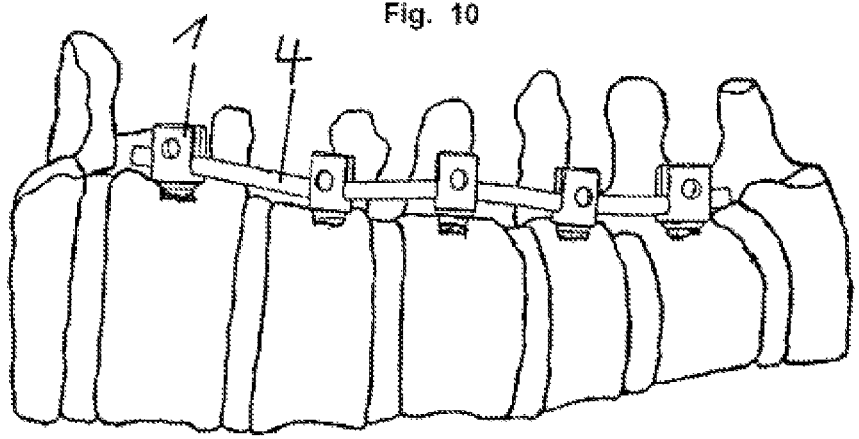
FIG. 10 shows an embodiment of the device according to the invention for the stabilization of the spine.

The design of the ball head 17 in the form of a ball having two opposite parallel surfaces referred to as 18a and 18b according to the invention is represented in FIG. 9. These surfaces 18a and 18b which abut on the respective parallel surfaces 18c and 18d of the screw head 3 prevent a rotational movement about the axial axis and only permit a tilting movement of up to 45°, preferably up to 30°, starting from the central position in respectively one lateral direction.

Figure 5:
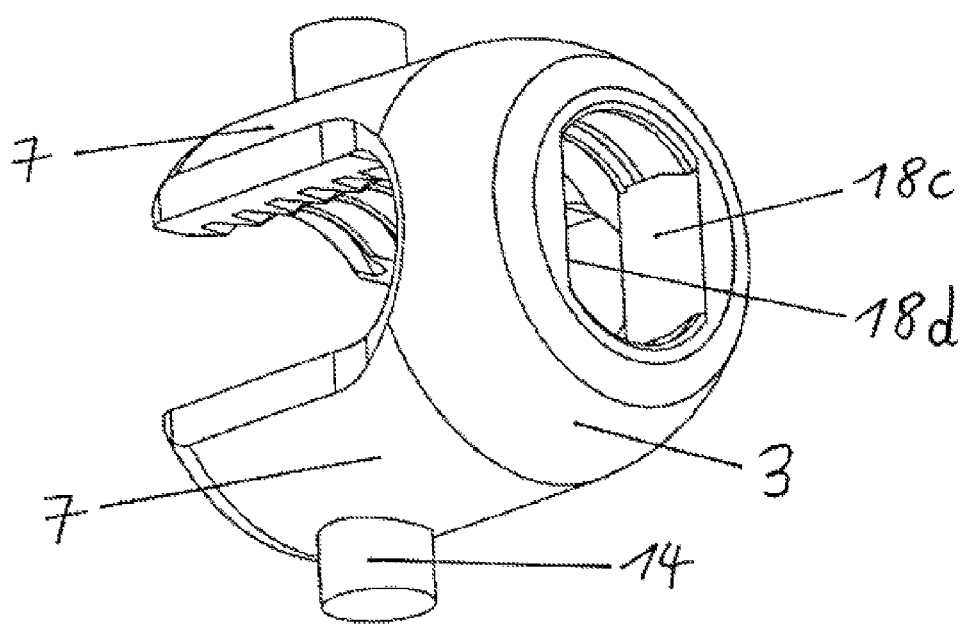
FIG. 5 shows the hollow screw head 3 of the pedicle screw 1 in U-shaped design with the two legs 7, at the bottom of the screw head 3, the elongated recess with two sides being parallel to each other (18c, 18d) for receiving the respectively designed ball head 17 of the screw shank can be seen.

The parallel surfaces 18c and 18d can be well seen in FIG. 5.

The parallel surfaces 18c and 18d are disposed on the lower extremity of the screw head 3 which is faced to the screw shank 2, as shown in FIG. 5. The thread in the screw head 3 does not extend to this area. The diameter of the shaft of the screw shank 2 is lower than the distance between the parallel surfaces 18c and 18d, so that the screw shank 2 can be introduced into the lower opening of the screw head 3 until the parallel surfaces 18a, 18c as well as 18b and 18d abut on each other, and the ball head 17 forms the bottom for receiving the ball element 6.

On the one hand, this limited movement is very important for optimally repositioning the vertebrae, and on the other hand, for strongly enclosing the linking member 4 in the fixation by the fixation means 5. The pedicle screws according to the invention combine in a clever way the advantages of a monoaxial screw with those of a polyaxial screw by simultaneously avoiding the disadvantages of both screw types. The pedicle screw according to the invention serves as a monoaxial screw in the implantation, i.e. it permits an optimal reducibility and possesses the advantages of a polyaxial screw when the linking member is introduced, which considerably facilitates the introduction and fixation of the linking member without the need for achieving this advantage only by reducing its reducibility.

The normal shape of a traumatized spine is restored and maintained by means of a fixator. This is achieved by the surgeon introducing the pedicle screw into the pedicle of the vertebra and reducing the vertebra to its optimal position by means of the screw, which serves as a lever. This recovery of the respective optimal position (reducibility) of the vertebrae is best achieved by means of monoaxial screws. Due to the rigid screw head in monoaxial screws, it is sometimes difficult to enclose the linking member 4 completely and immovably, so that maximal precision is required during implantation. However, if the screw head is supported in a polyaxial way, the screw head can adjust to the position of the linking member 4 and strongly lock the same. Unfortunately, this mobility of the screw head involves the drawback of the vertebrae not being able to be reduced in an optimal manner. Polyaxial screws are generally coupled to the thread rod, i.e. the screw shank of the pedicle screw, by being supported such that it is movable in all directions by means of a ball-shaped reception device of the screw head.

Thus, if the screw head is supported polyaxially, the possibility of using the pedicle screw as a lever for reducing the vertebra to its optimal position is limited, because the leverage effect is not, or only insufficiently, transmitted to the shank axis of the pedicle screw. Monoaxial pedicle screws do offer this possibility, but have other drawbacks, such as for example the fact that they require very exact and time-consuming work while forming the stabilization rod (linking member 4). Depending on the indication, there exists a distribution of 50% to 50% in the surgeons' selection of monoaxial or polyaxial systems.

The monoaxial screw sometimes cannot strongly enclose a linking member 4 once the fixation has been effected and furthermore requires a very high precision during the implantation, but offers the advantage of an optimal ability of reduction of the vertebrae. The polyaxial screw however provides a strong enclosure of the linking member 4 if the implantation of the individual pedicle screws has been effected in a less precise manner, with the drawback of an only suboptimal reducibility of the vertebrae due to the mobility, which is still present after the implantation, of the screw head.

The embodiments according to the invention achieve a strong enclosure or locking of the linking member 4 (stabilization rod) during the fixation by means of the ball element 6, i.e. the ball-shaped reception device for the linking member 4, wherein during the implantation the desired mobility is provided so that the implantation of the pedicle screws can be achieved more easily because no throughgoing precision is needed and still the reducibility (the reposition) of a monoaxial screw is maintained, because due to the immobility of the screw head, in particular along the critical axial axis, the complete leverage can be transmitted to the shank axis of the pedicle screw.

In very preferred embodiments of the present invention, the screw head 3 is as well supported such that it is movable on the screw shank 2, but is not movable in every direction or pivotable about 360°, as in polyaxial screws. According to the invention, the screw head 3 is placed on the screw shank 2, which has a ball head 17 with flattened sides 18a and 18b so that the screw head 3 is only pivotable about the axial axis (see FIGS. 5+9). This mobility combined with that of the ball element 6 provides the pedicle screw, and thus the complete device, with the mobility required for a strong, immovable support of the linking member 4 in the unfixed state, said mobility being combined with the rigidity required for an optimal reducibility of the vertebrae.

Holding means 14 can be attached to the screw head 3 of the pedicle screw 1 in the form of pins, curvatures, notches or recesses for setting a tool for screwing or a holding instrument.

For an easier introduction of the ball element 6 into the screw head 3, it is furthermore preferred that the screw head 3 has no through bore along the axial axis, but a recess that is open to the upper side. Furthermore, it is advantageous for facilitating the support and fixation of the ball element 6 that the screw head 3 has a bore along the axis of the screw shank 2, the internal diameter of which corresponds to a large extent to the external diameter of the ball element 6. The bore provides a centered opening in the screw head 3 on the side opposite the screw shank 2, which is suitable for receiving a fixation means 5.

FIG. 5 shows the screw head 3 of the pedicle screw 1 with the internal bore and the U-shaped recess, which after the insertion of the pedicle screw 1 into a vertebral body should pass along the spinal axis, i.e. the axial axis. In the preferred embodiments, the screw head 3 has two semicircular opposite legs 7 between which the ball element 6 with the throughgoing linking member 4 can be supported. In one preferred embodiment, the screw head 3 has a recess at the bottom which has two semicircular opposite sides and two sides being parallel to each other. A ball head with two surfaces being respectively parallel to each other is introduced into this recess such that only a tilting movement, but no rotational movement, of the screw head 3 on the screw shank 2 is possible.

As a ball element 6, any element pivotable about the lateral axis can be used. Balls having a centered through bore for reception of the linking member 4 are advantageous. In particular, two-piece ball elements 6 are preferred, which consist for example of a lower olive 8 faced to the screw shank 2 and of an upper olive 9 faced to the fixation means. The olives 8 and 9 have an internal diameter which is preferably equal to the external diameter of the linking member 4. Furthermore, the olives 8 and 9 preferably have an external diameter which is equal to a large extent to the internal diameter of the bore in the screw head 3 in direction of the longitudinal axis of the screw shank 2.

In another preferred embodiment, the supporting surfaces 15 and 16 of the two olives 8 and 9 are not plane-parallel but form an angle.

Figure 6:
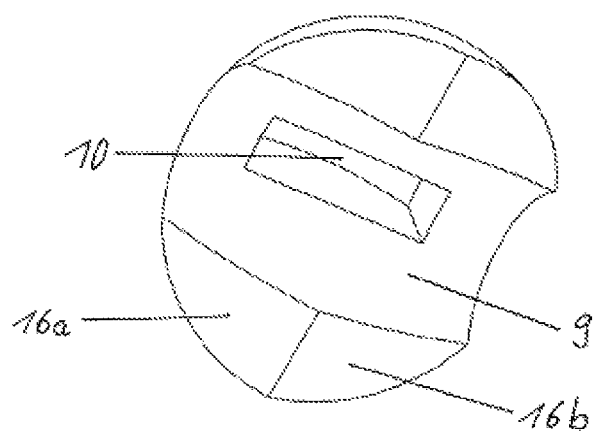
FIG. 6 shows a possible design of an upper olive 9 as part of a ball element 6; the lower olive has a design similar to that of the upper olive but without recess 10.

FIG. 6 shows a possible embodiment of the upper olive 9 with beveled supporting surfaces 16 for the lower olive 8. The two partial surfaces 16a and 16b of the support surface 16 comprise an angle of 100° to 190°, preferably of 110 to 180 degrees, and particularly preferable of 115 to 175 degrees. The lower olive 8 has the same shape as the upper olive 9, but has no recess 10. The two partial surfaces 15a and 15b of the supporting surface 15 of the lower olive 8 can comprise an angle of 100° to 190°, preferably of 110 to 180 degrees, and particularly preferable of 115 to 175 degrees. In a preferred embodiment, the lower olive 8 abuts on the ball head 17 of the screw shank 2.

The internal surfaces of the ball element 6 or respectively the internal surfaces of the lower olive 8 as well as of the upper olive 9, which abut on the linking member 4, can have a rough or an uneven surface structure for strongly locking the linking member 4 and for avoiding translational movements of the linking member 4 within the ball element 6 after the implantation.

In the preferred embodiments of the pedicle screw 1 with a bore in the screw head 3 in direction of the longitudinal axis of the screw shank 2, it is necessary to secure the ball element 6 by means of a fixation means 5. As a fixation means can be used pins, bolts, rods, wedges or other means fixating the ball element 6 within the screw head 3. Thread screws or threaded pins have proven to be particularly advantageous as fixation means 5. Thus, it is further preferred that the bore in the screw head 3 be a tap hole at least in the upper part. By means of the fixation means 5, the linking member 4 is strongly and immovably locked and enclosed in the ball element 6, respectively. Once the fixation has been effected, in particular after tightening the thread screws, the device according to the invention is fixed in its position so that the elements of the individual pedicle screws, which until then have been movable, are maintained as rigid and immovable elements in their respective position. The mobility of the device in this state is exclusively based on the flexibility of the linking member 4.

Figure 7:
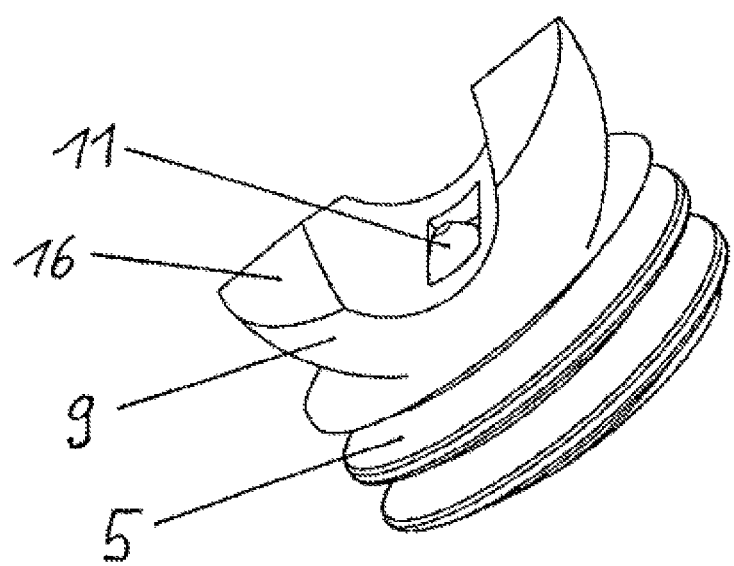
FIG. 7 shows an embodiment of the upper olive 9 as part of the ball element 6 which abuts on the fixation means 5.
Figure 8:
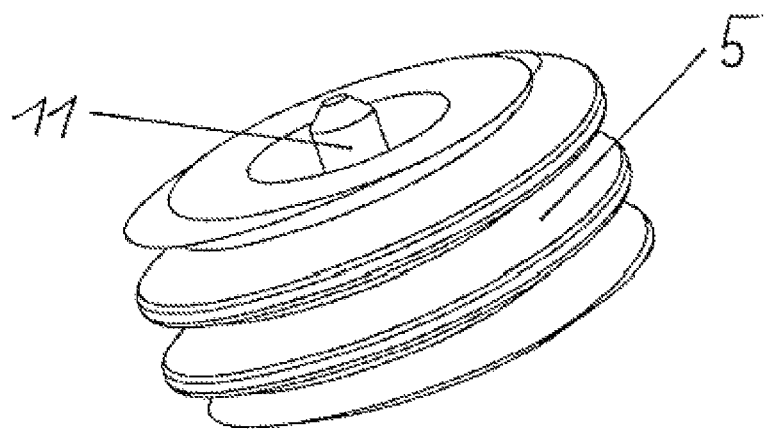
FIG. 8 shows a fixation means 5 in form of a threaded pin.

FIG. 8 shows a preferred fixation means 5 according to the invention in the form of a thread screw or a threaded pin, which has a recess 12 in its head for setting a screwing tool. In the concrete case, a hexagon recess for the use of a hexagon screw key is provided. The fixation means 5 further preferably has a guide pin 11 on its tip, which is movable due to its sliding within a respective recess in the ball element 6, preferably in the upper olive 9. FIG. 7 shows the way the upper olive 9 abuts on the fixation means 5 and the way the guide pin 11 engages the respective recess in the upper olive 9 at the fixation means 5.

Figure 4:
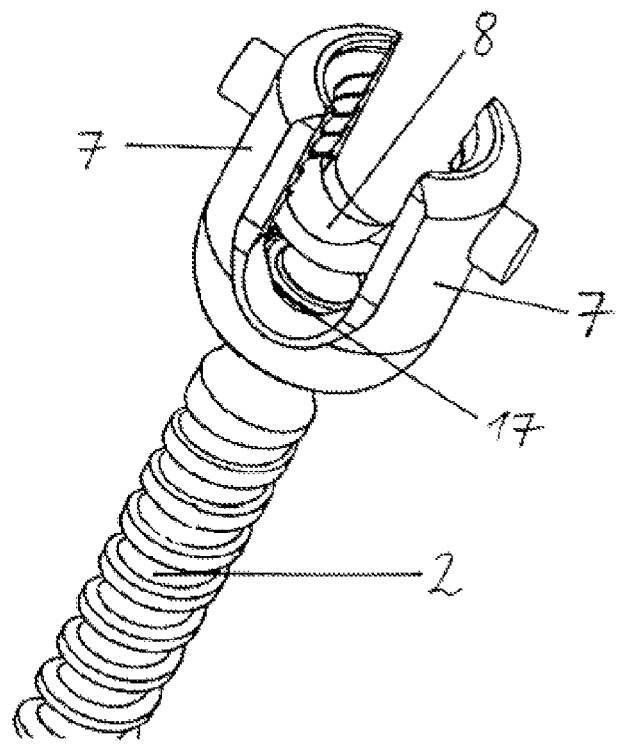
FIG. 4 shows the screw head 3 of the pedicle screw 1 with inserted lower olive 8 as part of the ball element 6 as well as one of the two flattened sides of the head 17 of the screw shank 2.

FIG. 4 shows the screw head 3 with inserted lower olive 8. In order to facilitate the swivelling movements of lower olive 8 about the lateral axis, it is preferred to support the lower olive 8 or the ball element 6 at the bottom of the screw head 3 on a central convex curvature 13. Thus, the screw head 3 preferably has a centered convex curvature 13 on the side faced to the screw shank 2 which is in particular formed as a hemisphere and which serves as a punctual support surface for the ball element 6 or the lower olive 8. In the particularly preferred embodiments with a screw head 3 movable in direction of the lateral axes, this convex curvature 13 is the ball head 17.

Figure 3:
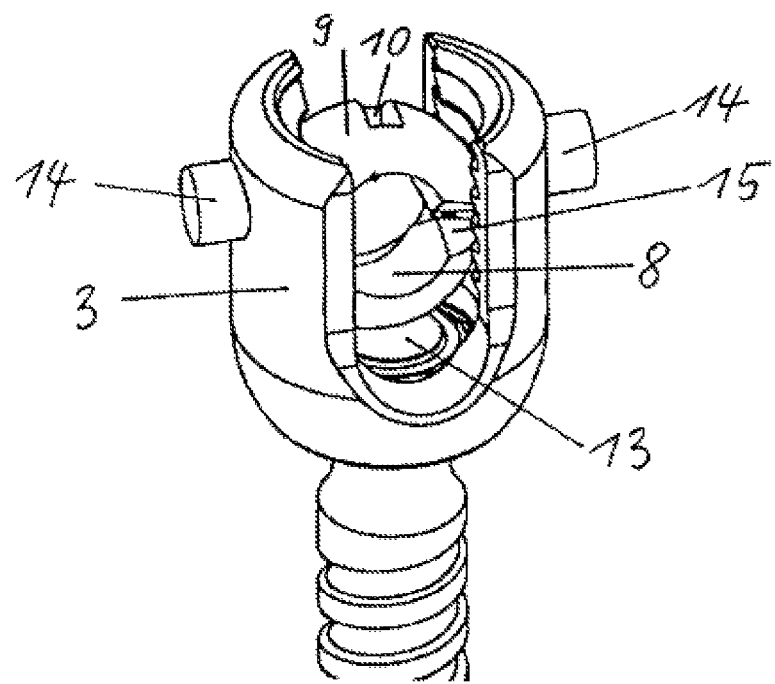
FIG. 3 shows the screw head 3 of the pedicle screw 1 with inserted ball element 6.

A screw head 3 according to the invention with inserted ball element 6 in the form of a lower olive 8 and an upper olive 9 is shown in FIG. 3. The cylindrical through bore in the ball element 6 extends through the two elongated hole-shape recesses in the screw head 3.

Figure 2:
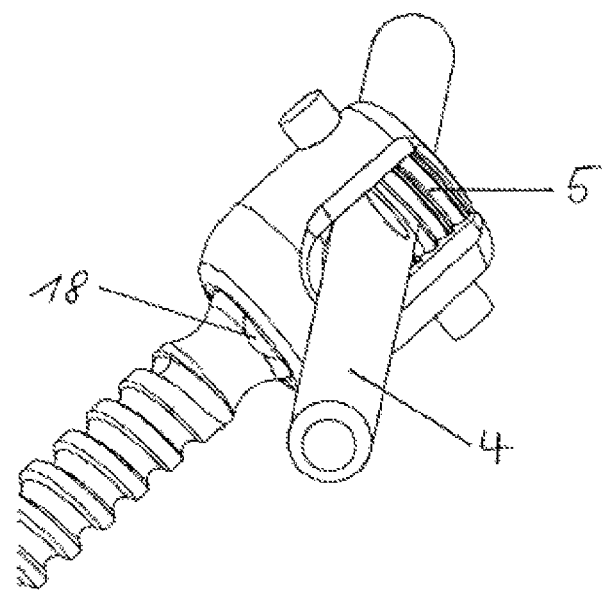
FIG. 2 shows a view of the pedicle screw 1 along the longitudinal axis of the linking member 4.

When the linking member 4 is introduced into the through bore in the ball element 6, the linking member 4 in the elongated hole of the screw head 3 can move about the lateral axis as long as the linking member 4 and thus, the ball element 6, are not fixed in their respective position by the fixation means 5. Once the linking member 4, which is introduced in the through bore in the ball element 6, has been fixed, enclosed or clamped in the screw head 3 by means of the fixation means 5, FIG. 2 shows clearly that the linking member 4 can no longer move in the elongated hole of the screw head 3 and is strongly locked or clamped. A rotational or turning movement about the lateral axis is no longer possible in the fixed state. The same applies to screw head 3, which is movably supported along the lateral axis on the screw shank 2. Further, translational movements along the spine axis, i.e. along the axial axis, are no longer possible in the fixed, enclosed or clamped state.

As materials for the pedicle screws 1 according to the invention can be used: medical special steel, titanium or titanium alloys, tantalum, chrome, cobalt-chrome-alloys, vanadium, tungsten, molybdenum, plastics such as PEEK (polyetherether ketone) as well as fiber-reinforced plastics.

As linking members 4 can be used support rods, tubes, wire nettings, guide bars or guide pins. It is further preferred that the at least one linking member 4 is curved or flexible for being adapted to the spine.

As materials for the at least one linking member 4 can be used: medical special steel, titanium or titanium alloys, tantalum, chrome, cobalt-chrome-alloys, vanadium, tungsten, molybdenum, plastics such as PEEK (polyetherether ketone) as well as fiber-reinforced plastics.

Further, it is preferred that the individual elements of the pedicle screw 1 according to the invention or at least the contact surfaces thereof are coated with a ceramic coating. Ceramic coatings comprise nitrides, carbides and phosphides of preferably metalloids and metals or metal alloys. Examples for ceramic coats are boron nitrides, titanium-niobium-nitride, titanium-calcium-phosphide (Ti—Ca—P), Cr—Al—N, Ti—Al—N, Cr—N, TiAlN—CrN, Ti—Al—C, Cr—C, TiAlC—CrC, Zr—Hf—N, Ti—Hf—C—N, Si—C—N—Ti, Si—C—N as well as DLC (Diamond Like Carbon). Further, a ceramic layer of titanium-niobium-nitride (Ti—Nb—N) is preferably applied as a coating.

It is in particular advantageous if the contact surfaces of the individual components are coated with titanium-niobium-nitride (Ti—Nb—N). A ceramic coat of titanium-niobium-nitride possesses a hardness which is much higher than that of conventionally used materials. Due to that hardness, the surface can be highly polished and is protected against titanium abrasion.

Furthermore the present invention relates to a device for the stabilization of the spine which consists of a plurality, but at least two, pedicle screws 1 according to the invention and at least one linking member 4.

The device for the stabilization of the spine according to the invention not only can be used for stabilizing two adjacent vertebral bodies with an interjacent intervertebral disc, but can also be attached over several vertebral bodies for supporting larger portions of the spine.

Generally at least 2 pedicle screws are in contact and are coupled by the linking member 4, i.e. by a stabilization rod. Thus, the spine is stabilized (corrected, if necessary) by external elements. Traumatized or degeneratively modified vertebrae are reduced and maintained in corrected position in their spatial arrangement by the spine fixator. Apart from the intrinsic flexibility of the linking member 4 (stabilization rod), the traumatized (or degenerated) proportion of the spine is fixed for the most part, so that the spine itself can serve as a support even if damaged structures exist. Said damaged structures are thus relieved and a repeated mispositioning is avoided.

Preferred embodiments of the pedicle screw or of the device according to the invention will now be discussed on the basis of the examples, wherein it is to be understood that the discussed examples show advantageous embodiments of the invention, however, the scope of the invention shall not be limited to these embodiments.

EXAMPLE 1

A pedicle screw 1 with a total length of 25-60 mm is provided. The pedicle screw 1 consists of titanium. Its screw shank 2 possesses a length of 15-45 mm adapted to that of the pedicle screw and an external diameter of 13-15 mm The screw head 3 has an external diameter of 17-20 mm.

The screw head 3 has an oval design and has a centered bore being 10-13 mm deep in the direction of the longitudinal axis of the screw shank 2, said axis being designed as a tap hole in the upper region of the screw head 3. The internal diameter of said bore is 6-8 mm.

The ball head 17 of the screw shank 2 is not designed as a complete ball but as a ball having two parallel opposite surfaces (18a, 18b) which correspond to the respective surfaces 18c and 18d of the screw head 3 and determine the mobility thereof or respectively, prevent a free rotatability. The parallel opposite surfaces 18a as well as 18b respectively possess a surface of about 0.7 cm$^2$.

The screw head 3 further has a through bore which is open to the top side and elongated hole-shape and which is designed round at the bottom of the screw head 3 which has a diameter which corresponds to a large extent to the diameter of the linking member 4 to be introduced.

At the bottom of the screw head 3, a hemispherical convex curvature 13 on which the lower olive 8 abuts, is present. Internal diameters of the lower olive 8 as well as of the upper olive 9 correspond to a large extent to the external diameter of the linking member 4 to be introduced.

The upper olive 9 is placed on the lower olive 8, the support surfaces 15a, 15b or respectively 16a, 16b of both olives comprise an angle of 150°.

The upper olive 9 has an elongated recess 10 along the axial axis, which receives the guide pin 11 of the fixation means 5. The guide pin 11 has a length of 1-3 mm and an external diameter of 0.5-2 mm.

On the upper olive 9, the fixation means 5 in form of a threaded pin is placed. A guide pin 11 is arranged on the lower head of the threaded pin, and a recess is arranged in its head for receiving a tool for screwing in the same.

The threaded pin has a thread corresponding to the tap hole in the screw head 3 and can be screwed into the screw head 3 until it strongly locks the linking member 4 between the upper olive 9 and the lower olive 8.

As linking member 4 serves a flexible tube of medical special steel, titanium, titanium alloys or tantalum, with a variable length of 4 cm up to 30 cm and with an external diameter of 3-8 mm.

The linking member 4 cannot move translationally along the spine axis, but, as long as it is not fixed yet, it can make a rotational movement of up to 12 degrees, preferably up to 24 degrees about the lateral axis, starting from a horizontal position which is perpendicular to the longitudinal axis of the screw shank.

The individual components of the pedicle screw 1 are preferably provided with a ceramic coat.

EXAMPLE 2

A pedicle screw 1 with a total length of 45 mm is provided. The pedicle screw 1 consists of tantalum. Its screw shank 2 possesses a length of 35 mm which is adapted to that of the pedicle screw and an external diameter of about 14 mm. The screw head 3 has an external diameter of about 18 mm.

The screw head 3 has an oval shape and possesses a centered bore being 12 mm deep in the direction of the longitudinal axis of the screw shank 2, said axis being designed as a tap hole in the upper region of the screw head 3. The internal diameter of said bore is about 7 mm.

The ball head 17 of the screw shank 2 is not designed as a complete ball but as a ball having two parallel opposite surfaces (18a, 18b) which correspond to the respective surfaces 18c and 18d of the screw head 3 and determine the mobility thereof or respectively, prevent a free rotatability. The parallel opposite surfaces 18a as well as 18b respectively possess a surface of about 0.55 cm$^2$.

The screw head 3 further has a through bore which is open to the top side and elongated hole-shape and round at the bottom of the screw head 3, which has a diameter which corresponds to a large extent to the diameter of the linking member 4 to be introduced.

The screw shank 2 has a ball head 17, said ball head 17 having two opposite parallel surfaces 18a and 18b. The screw head 3 has a respective recess for receiving the ball head 17 and is supported such that it is movable in lateral direction on the screw shank 2. The screw head 3 can be inclined up to 30 degrees starting from the centered position in lateral direction. Thus, the bottom of the screw head 3 is formed by the ball head 17 on which the lower olive 8 abuts. The internal diameter of the lower olive 8 as well as of the upper olive 9 correspond to a large extent to the external diameter of the linking member 4 to be introduced.

The upper olive 9 is placed on the lower olive 8, the support surfaces 15a, 15b or respectively 16a, 16b of both olives comprising an angle of 140°.

The upper olive 9 has an elongated recess 10 along the axial axis, which receives the guide pin 11 of the fixation means 5. The guide pin 11 has a length of 1-3 mm and an external diameter of 0.5-2 mm.

On the upper olive 9, the fixation means 5 in form of a threaded pin is placed. The guide pin 11 is arranged on the lower end of the threaded pin, and a recess is arranged in its head for receiving a tool for screwing in the same.

The threaded pin has a thread corresponding to the tap hole in the screw head 3 and can be screwed into the screw head 3 until it strongly locks the linking member 4 between the upper olive 9 and the lower olive 8.

A flexible tube of medical special steel having a length of 25 cm and an external diameter of 6 mm serves as linking member 4.

The linking member 4 cannot move along the spine axis with a translational movement, but, as long as it is not yet fixed, it can make a rotational movement of up to 12 degrees, preferably up to 24 degrees about the lateral axis, starting from a horizontal position which is perpendicular to the longitudinal axis of the screw shank.

The individual components of the pedicle screw 1 are preferably provided with a ceramic coat.

EXAMPLE 3

A device according to the invention for the stabilization of the spine consists of 5 pedicle screws 1 and one linking member 4 with a total length of 13 cm.

This device can be attached over a total of 5 vertebrae.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. Pedicle screw (1), comprising a screw shank (2) with a ball head (17) as well as a screw head (3) having two opposite recesses, characterized in that the ball head (17) has two opposite parallel surfaces (18a, 18b) which abut on corresponding parallel surfaces (18c, 18d) of the screw head (3) and in that a longitudinal axis passes through the two opposite recesses of the screw head (3) perpendicular to the parallel surfaces (18c, 18d) of the screw head (3) and in that the screw head (3), which is supported on the screw shank (2), cannot freely rotate about the longitudinal axis of the screw shank (2), a fixation means (5), a ball element (6) with a recess for receiving a linking member (4) that is supported such that it is movable in the screw head (3), wherein the ball element (6) consists of two olives (8,9) supported on each other, having an internal diameter which is preferably equal to the external diameter of the linking member (4), having an external diameter which is substantially equal to the internal diameter of a bore in the screw head (3) in a direction parallel to the longitudinal axis of the screw shank (2), and the lower olive (8) is facing the screw shank (2) and the upper olive (9) is facing the fixation means (5), wherein the screw head (3) has an opening for receiving the fixation means (5) on the side which is opposite the screw shank (2), a tip of the fixation means (5) has a guide pin (11), and the upper olive (9) facing the fixation means (5) has a recess (10) for receiving the guide pin (11) of the fixation means (5).

2. Pedicle screw according to claim 1, characterized in that the ball element (6) has a bore along an axis which passes through the two opposite recesses.

3. Pedicle screw according to claim 1, characterized in that the screw head (3) is supported on the ball head (17) of the screw shank (2) such that the screw head (3) can make one-dimensional tilting movements about the axial axis.

4. Pedicle screw according to claim 1, characterized in that the screw head (3) has a convex curvature (13) on a side facing the screw shank (2).

5. Pedicle screw according to claim 1, characterized in that the fixation means (5) is a threaded pin.

6. Device for the stabilization of the spine comprising at least two pedicle screws (1), each pedicle screw comprising a screw shank (2) with a ball head (17) as well as a screw head (3) having two opposite recesses, characterized in that the ball head (17) has two opposite parallel surfaces (18a, 18b) which abut on corresponding parallel surfaces (18c, 18d) of the screw head (3) and in that a longitudinal axis passes through the two opposite recesses of the screw head (3) perpendicular to the parallel surfaces (18c, 18d) of the screw head (3) and in that the screw head (3), which is supported on the screw shank (2), cannot freely rotate about the longitudinal axis of the screw shank (2), a fixation means (5), a ball element (6) with a recess for receiving a linking member (4) that is supported such that it is movable in the screw head (3), wherein the ball element (6) consists of two olives (8,9) supported on each other, having an internal diameter which is preferably equal to the external diameter of the linking member (4), having an external diameter which is substantially equal to the internal diameter of a bore in the screw head (3) in a direction parallel to the longitudinal axis of the screw shank (2), and the lower olive (8) is facing the screw shank (2) and the upper olive (9) is facing the fixation means (5), wherein the screw head (3) has an opening for receiving the fixation means (5) on the side which is opposite the screw shank (2), a tip of the fixation means (5) has a guide pin (11), and the upper olive (9) facing to the fixation means (5) has a recess (10) for receiving the guide pin (11) of the fixation means (5), and at least one linking member (4).

7. Device according to claim 6, wherein the at least one linking member (4) is a support rod, tube, wire netting, guide bar or a bent guide rod.

* * * * *